United States Patent [19]

Shasha et al.

[11] Patent Number: 4,859,377
[45] Date of Patent: Aug. 22, 1989

[54] STARCH ENCAPSULATION OF ENTOMOPATHOGENS

[75] Inventors: Baruch S. Shasha, Peoria; Richard L. Dunkle, Morton, both of Ill.

[73] Assignee: The United States of America, as represented by the Secretary of Agriculture, Washington, D.C.

[21] Appl. No.: 72,205

[22] Filed: Jul. 10, 1987

[51] Int. Cl.[4] .................. B01J 13/02; C12N 11/10
[52] U.S. Cl. ...................... 264/4.1; 424/410; 424/488; 435/178; 514/965
[58] Field of Search ............... 264/4.1 APS; 424/410, 424/488; 514/965; 435/178

[56] References Cited

U.S. PATENT DOCUMENTS

| 1,677,615 | 7/1928 | Boidin et al. | 435/178 |
|---|---|---|---|
| 3,223,593 | 12/1965 | Aldrich et al. | 435/182 X |
| 3,499,962 | 3/1970 | Wurzburg et al. | 424/35 |
| 3,971,852 | 7/1976 | Brenner et al. | 424/488 X |
| 4,418,147 | 11/1983 | Muetgeert et al. | 435/178 |
| 4,450,233 | 5/1984 | Mimura et al. | 435/178 |
| 4,657,582 | 4/1987 | Huber | 424/410 X |
| 4,713,241 | 12/1987 | Wakisaka et al. | 424/93 |
| 4,752,468 | 6/1988 | Kennedy et al. | 424/93 |
| 4,755,397 | 7/1988 | Eden et al. | 424/488 X |
| 4,812,445 | 3/1989 | Eden et al. | 514/60 |

FOREIGN PATENT DOCUMENTS 2036032  6/1980  United Kingdom ............... 435/178

*Primary Examiner*—John F. Terapane
*Assistant Examiner*—Gary Geist
*Attorney, Agent, or Firm*—M. Howard Silverstein; Curtis P. Ribando; John D. Fado

[57] ABSTRACT

Biological control agents such as pathogenic bacteria and viruses have been encapsulated in a protective, starch matrix without the use of chemical crosslinking agents. The agent is blended into a dispersion of pregelatinized starch, which is thereafter subjected to conditions suitable for retrogradation. Dispersions can be formulated either for recovery of dry granules or as sprayable liquids. Encapsulated products are useful in controlling insects and other pest species having chewing mouth parts and amylase digestive enzymes.

10 Claims, No Drawings

STARCH ENCAPSULATION OF ENTOMOPATHOGENS

BACKGROUND OF THE INVENTION

1. Field of the Invention

Encapsulation is rapidly becoming a major technology for formulating bioactive agents. Encapsulation has significantly extended field life of agricultural pesticides by offering protection from environmental exposure and resultant chemical and biological degradation. Moreover, it has allowed application of many pesticides at reduced dosages and less frequent intervals, thus reducing environmental contamination and extending residual activity.

Encapsulation technology similar to that developed for chemical pesticides could be useful to protect entomopathogens such as *Bacillus thuringiensis* (B.T.), nuclear polyhedrosis viruses, microsporidians, and other biocontrol agents. Most biocontrol agents are susceptible to rapid environmental degradation caused by exposure to ultraviolet radiation, heat, desiccation, substrate pH, and microbial competition, which severely limits their practical utility.

Economically feasible formulation technology that provides long-term protection of biocontrol agents from environmental degradation and also promotes infection of the target pest is critically needed to further their use in applied pest control. This invention relates to a novel encapsulation system which satisfies these criteria.

2. Description of the Prior Art

Techniques, including the use of clay granules [E. S. Raun et al., J. Econ. Entomol. 59: 620–622 (1966); S. M. Ahmed et al., Pestic. Sci. 4 19–23 (1973)], UV-absorbing compounds [R. P. Jaques, Can. Entomol. 104: 1985–1994 (1972); D. L. Hostetter et al., J. Kansas Entomol. Soc. 48: 189–193 (1975)] and encapsulation, have been developed for short-term environmental protection of entomopathogens. In the latter case, microencapsulation of nuclear polyhedrosis viruses with polyvinyl alcohol, ethylcellulose, or other polymers, coupled with UV-screening agents has been achieved [C. M. Ignoffo et al., J. Econ. Entomol. 64: 850–853 (1971); D. L. Bull et al., J. Econ. Entomol. 69: 731–736 (1976)]. However, field studies with these formulations produced variable results in the degree of pathogen survival and efficacy against the target insect. Calcium alginate used to encapsulate steinernematid and heterorhabditid nematodes offers promise, although the ability of the alginate to maintain moisture conditions conducive to nematode survival was a problem [H. K. Kaya et al., Environ. Entomol. 14: 572–574 (1985)].

The use of starch has many attractive properties for biocontrol agent encapsulation. First, it is inert and will not alter resting stages of most living organisms; second, particulate or liquid UV-screening agents are easily added; third, its major component is amylopectin which is readily digested by most phytophagous pests possessing α-amylase enzymes [G. M. Chippendale et al., J. Insect Physiol. 20: 751–759 (1974); K. Nishide et al., J. Fac. Agric. Tottori Univ. 11: 12–22 (1976)]; and fourth, it is abundant and inexpensive compared to most other materials currently used in encapsulation [B. S. Shasha, In Controlled Release Technologies: Methods, Theory, and Applications, Vol. 2, A. F. Kydoniens (ed.), CRC Press, Inc., Boca Raton, FL].

Recently, pesticides have been encapsulated in starch, crosslinked with borate, calcium, or xanthide, thereby producing a matrix that can be processed into granules of desired sizes, densities, and porosity [B. S. Shasha et al., J. Appl. Polym. Sci. 29: 67–73 (1984); D. Trimnell et al., J. Polym. Sci. 27: 3919–3928 (1982); R. E. Wing et al., J. Polym. Sci. 21: 121–140 (1983)]. Unfortunately, this encapsulating process is not suited for most biocontrol agents because the reagents and conditions of the crosslinking process are too harsh for their survival.

Controlled release by means of starch-based encapsulating materials can also be accomplished without the use of chemical crosslinking reactions. In U.S. Patent No. 2,876,160, Schoch et al. disclose such a method which employs modified, amylose-free starches at concentrations up to 65% solids for embedding water-insoluble materials.

In PCT Int. Appl. WO 85/04074, Flashinski et al. disclose two methods of preparing a starch gel matrix containing an insecticide. The insecticide is either coextruded with a dilute, aqueous dispersion of starch, or the starch is first partially cooked in an extruder prior to cold-blending with the insecticide. In either case, the product is recovered and used as an aqueous gel.

In U.S. Pat. No. 4.230,687, Sair et al. disclose the application of shearing stress, vigorous mechanical working, and heat to distribute active agent into an enveloping matrix of chemically modified starches, gums, and proteins in the presence of a limited quantity of water. Proteins are used for slow-release matrices; modified starches are used for rapid release.

Similarly, in U.S. Pat. No. 3,922,354, Galuzzi et al. disclose the use of high-shear mixing to incorporate active agents into low-water, high-solids matrices prepared from partially gelatinized unmodified starches. Additives such as modified dextrins, mixtures of mono- and diglycerides, toasted cereal solids, and coloring agents are used to control the release of active agents.

In U.S. Pat. No. 3,666,557, Jensen et al. disclose a method of using low-fat starchy materials to microencapsulate individual beadlets of sensitive materials such as vitamins and vegetable oils. Starches are prepared for encapsulation by heating at 88° C. for 30 min followed by passage through a homogenizer to effect disruption of granules without degradation of molecules.

SUMMARY OF THE INVENTION

We have now unexpectedly discovered a method of achieving substantially complete encapsulation of virtually all types of biocontrol agents in a starch system under nondestructive conditions without the use of chemical crosslinking reagents. The agents are blended into an aqueous dispersion of amylose-containing, pregelatinized starch, in which reassociation of amylose molecules occurs upon dispersion in an aqueous system. This reassociation forms a continuous, insolubilized matrix entrapping discontinuous domains of the agent within the interstices of the reassociated chains.

In accordance with this discovery, it is an object of the invention to provide a facile, universal, and industrially acceptable method for encapsulation of sensitive biocontrol agents.

It is also an object of the invention that the primary matrix-forming material be derived from natural renewable resources.

Another object of the invention is that the method of encapsulation be characterized by high survivability of the active agent.

It is a further object of the invention to provide a versatile encapsulation system whereby the product applied to the field is either a free-flowing particulate or else a sprayable liquid.

Another object of the invention is to provide a product in which the encapsulated substance is sufficiently protected to be safe for handling, controllably released to a wide variety of environments, and resistant to losses by environmental conditions.

Other objects and advantages of this invention will become readily apparent from the ensuing description.

DETAILED DESCRIPTION OF THE INVENTION

Starch is a low-cost and abundant natural polymer composed of amylose and amylopectin. Amylose is essentially a linear polymer having a molecular weight in the range of 100,000–500,000, whereas amylopectin is a highly branched polymer having a molecular weight of up to several million. When starch is gelatinized in water and cooled, the amylose retrogrades to a much greater extent than the amylopectin fraction. Retrogradation is a term applied to the phenomenon whereby starch chains in dispersion associate, become insoluble, and precipitate. The rate and extent of retrogradation depend on properties of dispersion (pH, temperature, concentration) and on the amount of amylose present in the dispersion. Common cornstarch (pearl) contains about 25% amylose and 75% amylopectin; whereas the waxy corn starches contain only amylopectin, and those referred to as high-amylose starch contain up to 75% amylose.

The starting encapsulating material for use in the invention includes any pregelatinized starch which will retrograde to form a gel upon rehydration in an aqueous medium, and thereafter be amylase digestible. Pregelatinized starches are commercially available and are prepared for example by cooking the starch at elevated temperatures and pressures in the presence of a lower alcohol. It is preferred that the pregelatinized starch be cold-water-swelling, and especially preferred that it be chemically unmodified. An example of such a starch is disclosed by Eastman et al. in U.S. Pat. No. 4,465,702, herein incorporated by reference. The level of amylose in the starch must be above about 5%, below which the starch will not form a cohesive mass in the presence of water.

Though the product of Eastman et al. is derived from regular pearl cornstarch, it is understood that other natural granular starches could be pregelatinized for purposes of the invention. These would include the other cereal starches, potato starch, tapioca starch, flours containing these starches, as well as mixtures of these with waxy cornstarch and high-amylose cornstarch.

The biocontrol agents contemplated for use herein include without limitation all bacteria, fungi, yeasts, viruses, microsporidians, protozoa, and other lower organisms which are pathogenic toward target pests. Of course any component of the organism or stage of its life cycle which is infective to the host upon ingestion is considered to be within the scope of the invention. For instance, in the case of B.t., the vegetative cells, spores, and proteinaceous crystals are all effective in directly or indirectly killing host insects susceptible to B.t. It is also known that naturally occurring and synthetic vectors such as plasmids, phages, and various DNA/RNA constructs have potential for functionally modifying higher organisms, and therefore are also included herein as being within the scope of the term "biocontrol agent." Examples of other agronomically important pest pathogens besides B.t. are *B. sphaericus, B. popillae,* microsporidians such as *Vairimorpha necatrix* and *Nosema locustae, Autographa californica* nuclear polyhedrosis virus, and *Heliothis* spp. virus.

The target pests contemplated for control by means of the subject encapsulated agents include all species having chewing mouth parts and amylase digestive enzymes. These characteristics are typical of most phytophagous (plant-eating) insects, especially those considered to be crop or tree pests.

Besides the active agent itself, other additives and adjuncts may be formulated into the subject compositions. Examples of these include dispersants, feeding stimulants (phagostimulants), UV protectants, sticking agents, preservatives, and inert fillers. Also of interest are agronomically acceptable carriers or vehicles for the active agent or any of the other components formulated into the encapsulated compositions. We have found that corn oil in an amount of about 5–10% by weight serves to help disperse the biocontrol agent, minimize clumping of the pregelatinized starch, and also act as a mild phagostimulant for certain insects such as the European corn borer. Examples of UV screens include Congo-red, folic acid, paraminobenzoic acid, and azobenzene.

Encapsulation of the biocontrol agent into the starch matrix is initiated by uniformly dispersing the agent throughout an aqueous dispersion of the pregelatinized starch. The order of combining the various components of the formulation is not critical and may be conducted in whatever manner best facilitates the process. Under suitable gelation conditions, the starch which has been dispersed in an aqueous medium begins to retrograde, thereby forming a gelatinous mass. By proper formulation as described in more detail below, the dispersion will gel at room temperature within about 5–60 sec and can thereafter be taken to dryness. The reassociation of the amylose components of the starch results in a substantially homogeneous mass analagous to the precursive mixture in which, now, discontinuous domains of active ingredient are uniformly dispersed throughout a continuous starch matrix. This process distinguishes from microencapsulation which yields discrete particles, each comprising a domain of agent enveloped by a film or coating of encapsulating agent.

The relative amount of the starch solids with respect to the biocontrol agent should be sufficient to entrap the agent within a matrix of the starch. In preparing a granular product, it is preferred that the starch concentration be within the range of about 25–40% solids by weight, so as to promote rapid gelling. In order to preserve the viability of active agent, the temperature must be held below about 40° C. and the pH must be in the range of about 4–8.

The recovery procedure is aimed at converting the homogeneous mass to discrete, free-flowing, nonagglomerating particles. In accordance with one method of recovery contemplated herein, the gelled starch-agent mixture is placed on trays and allowed to stand for about 30 min at room temperature. The resultant, nonsticky mass is then ground by suitable means into nonagglomerating particles. Coating the mass with pearl cornstarch powder prior to grinding will facilitate particulation. Dry particles do not dissolve, encrust together or adhere to the surface to which they have been applied after exposure to water.

For purposes of this invention, the starch dispersion is considered to be in the aqueous phase, which will constitute the continuous phase of the encapsulation system. The domains of the active agent or other additive which constitute the discontinuous or dispersed phase of the mixture should be sufficiently small to render the mixture stable until the amylose components reassociate with one another and entrap the dispersed material. It would be within the skill of a person in the art to determine the maximum level at which a particular agent or additive can be effectively loaded into the system. An "effective amount" is defined herein as that amount of a component which will achieve the desired result (e.g., infect and kill pests, preserve the formulation, etc.).

Depending on the particular biocontrol agent, the target pest species, concentration of agent, and method of application, the subject encapsulated products act to control pests by one or more mechanisms, including, for instance, death inducement, feeding deterrency, growth regulation, sterilization, as well as interference with metamorphosis and other morphogenic functions. Accordingly, the level of active agent is administered in an amount effective to induce one or more of these responses as predetermined by routine testing. Where the ultimate response is pest mortality, a "pesticidally effective amount" is defined to mean those quantities of agent which will result in a significant mortality rate of a test group as compared to an untreated group. The actual amount may vary with the particular biocontrol agent, the species of pest, the stage of larval development, the type of vehicle or carrier, and other related factors.

To be effective, the agent must be applied to the locus of, or the vicinity of, the pest to be controlled. When the pest diet is a crop plant or tree, the composition will typically be applied to the foliage. In the presence of moisture, the starchy granules will reversibly swell without redispersing. Stability of both the biocontrol agent and the starchy matrix against environmental conditions can be tailored by incorporation of a variety of additives as previously discussed. The encapsulated agent can thereby be formulated to persist under field conditions until ingested by the target species, whereupon digestion of the starch matrix will release the agent into the digestive tract.

In an alternative embodiment of the invention, the biocontrol agent can be formulated into a sprayable liquid. In a sprayable formulation, the pregelatinized starch or flour in aqueous dispersion must have a low but stable viscosity of less than about 1000 cps. This property is characteristic of starches and flours which have been partially degraded by chemical or physical means to the extent that the amylose chains will not spontaneously reassociate until their concentration in dispersion is raised above that of the sprayable formulation. Thus, gel formation is retarded until evaporation of water from the sprayed composition causes the concentration of the degraded starch molecules to exceed a predetermined threshhold. Initial concentrations of the starch in the sprayable formulation should be in the range of about 1-10% by weight. In field application, droplets of the liquid adhere to the foliage surfaces and remain bound thereto even after gelling takes place.

In still another embodiment of the invention, we have found that by dispersing the encapsulating material in water in the presence of a polar organic solvent such as methanol, a portion of the aqueous solvent can be removed from the gelled product by filtration. Moreover, the recovered product will be in a very fine particulate or powdered form.

The following examples are intended only to further illustrate the invention and are not intended to limit the scope of the invention which is defined by the claims.

EXAMPLES 1-3

In order to evaluate the efficacy of the starch encapsulation system of the invention, refined corn oil ("Mazola") was encapsulated in the absence of a biocontrol agent in the following manner. The corn oil (2 g) was mixed with pregelatinized starch powder (25 g) produced under the tradename "Miragel 463" by A. E. Staley Manufacturing Company, Decatur, IL). Distilled water (60 ml) chilled to 2° C. was then stirred into the starch-oil mixture thereby forming a gelatinous mass within 10 to 15 sec. The mixture was allowed to stand for 30 min at room temperature, producing a nonsticky mass which was processed in a Waring blender with 25 g pearl starch powder to yield particles that passed a 14-mesh screen (1410 microns). After air drying for 24 hr at room temperature, the particles were sieved into various mesh sizes. The resulting particles contained domains of corn oil uniformly dispersed and entrapped within the pregelatinized starch matrix, which in turn was surrounded by a thin coating of pearl corn starch.

Encapsulation properties of the matrix were evaluated by assaying 2-g samples for the amount of oil retained in the final product after soaking with 50 ml chloroform for 30 min. The amount of oil which escaped encapsulation was determined by separating the chloroform solvent from the sample, evaporating the solvent, and weighing the residual oil. The extracted samples were then treated with α-amylase ("Termamyl 120") to release the encapsulated oil which was also taken up in chloroform. After removing the solvent, the encapsulated oil was weighed and the percent oil encapsulated computed. The results are reported in Table I below.

TABLE I

| | Oil Retention Efficiencies | |
| --- | --- | --- |
| Example | Formulation, % oil/starch by wt. | % Retention |
| 1 | 4 | 84 |
| 2 | 6 | 79 |
| 3 | 8 | 63 |

EXAMPLE 4

*Propagation of Bacillus thuringiensis (B.t.)*

*Bacillus thuringiensis* HDI (NRRL B-3792) was propagated by the method of Nickerson et al. [K. W. Nickerson et al., Appl. Microbiol. 28: 129-132 (1974)]except that a modified YMG medium containing yeast extract (0.5%), malt extract (0.5%), tryptone (0.5%), peptone (0.5%), glucose (0.5%), and $KHPO_4$ (0.1%) was used. This procedure yielded 350 g (wet weight) of cell paste containing B.t. spores and crystals which were stored at 2° C. until used.

Encapsulation Procedure

Laboratory samples of 50 to 55 g (dry weight) of encapsulated B.t. were prepared in the following manner: refined "Mazola" corn oil (2 g) was mixed with pregelatinized starch powder (25 g) produced under the tradename "Miragel 463" by A. E. Staley Manufacturing Company, Decatur, IL), distilled water (60 ml) chilled to 2° C. containing a suspension of 158 mg B.t. spores and crystals was then stirred into the starch-oil mixture thereby forming a gelatinous mass within 10 to 15 sec. The mixture was allowed to stand for 30 min at room temperature, producing a nonsticky mass which was processed in a Waring blender with 25 g pearl starch powder to yield particles that pass a 14-mesh screen (1410 microns). After air drying for 24 hr at room temperature, the particles were sieved into various mesh sizes. The resulting particles contained domains of B.t. spores and crystals at a level of 0.3% by weight entrapped within the pregelatinized starch matrix, which in turn was surrounded by a thin coating of pearl starch.

EXAMPLE 5

Selected granules of the encapsulated B.t. product of Example 4 were fixed in 2% glutaraldehyde in 0.1 M sodium phosphate buffer (pH 7.2) for 8 hr at room temperature. After washing overnight in buffer, they were post-fixed with 1% osmium tetraoxide in the same buffer for 4 hr., rinsed with water, dehydrated in an acetone series, and embedded slowly (over a 3-day period) in "Effa-poxy" resin. After polymerization, sections (2 μm) thick) were cut with glass knives, mounted on gelatin-coated slides, stained with toluidene blue O, mounted in "Permount" and photographed with a photomicroscope at 1200X. The photomicrographs revealed numerous developing B.t. parasporangia, spores and crystals randomly distributed throughout the particles.

Granules of the encapsulated B.t. product of Example 4 were soaked in distilled water for 24 hr. Microscopic examination of leachate revealed essentially no B.t. spores and crystals outside the granules, indicating that nearly all the B.t. remained entrapped.

EXAMPLES 6-16

Diet-Incorporated Assays

A premixed wheat germ, European corn borer (*O. nubilalis*) artificial diet (No. 9078, Bioserv, Frenchtown, NJ) was used in these assays. Preliminary information on infectivity of our laboratory-cultured B.t. was determined by incorporating unencapsulated spores and crystals into freshly made larval diet (cooled to 50°-55° C.) at the rates of 15 g B.t./g diet (LD50) and 50 g/g diet, respectively. Diet-B.t. mixture (15 ml) was dispersed into each 30-ml cup. After the diet had cooled, one neonate 2-3 hr old larva was transferred into each cup with a sterilized fine-haired brush, and the cup was capped with a wax-coated paper lid. All assays were conducted at 27° C. and 60% RH, and mortality was recorded at 7 days and/or 12 days.

Diet-incorporated assays were conducted with neonate European corn borer larvae to determine whether the encapsulation process was inactivating the spores and crystals. For Examples 6 and 7, B.t. spores were encapsulated as described in Examples 4 at a concentration of 0.2% by weight and a particle size of 12-20 mesh (1700-850 microns), and were incorporated into the diet at concentrations of 0.005% and 0.0015%. The results were compared in Example 8 to a blank without B.t. For Examples 9 and 10, samples of encapsulated B.t. at the same dosage levels as for Examples 6 and 7 were treated with 4 ml of 0.1% "Termamyl" amylase per gram matrix. Example 11 was a blank. Resultant liquefied matrices were incorporated into the diet and assayed as above. The results of Examples 6-11 were compared to the freely suspended B.t. in Examples 12-14. For Example 15, the procedure of Example 9 was repeated with B.t. encapsulated at a level of 0.3%. After a storage period of 4 mo at room temperature, the amylase-treated product was assayed in comparison to a blank (Example 16). The results of this series of experiments are reported in Table II below. It is apparent that the B.t. remains virulent after encapsulation. However, the results of Examples 6-8 suggest that, in the diet-incorporated assay, premixed components of the diet may have been preferentially available over the B.t.-encapsulated granules.

EXAMPLES 17-25

B.t. was encapsulated at a level of 0.3% by weight by the procedure of Example 4, and the recovered granules were screened to three mesh sizes. For each screen size, the encapsulated B.t. was incorporated in the European corn borer diet and assayed as described in Examples 6-16. The percent mortality at 7 and 12 days and the mean survivor weight at 12 days were recorded as shown in Table III.

EXAMPLES 26-31

B.t. was encapsulated at a level of 0.3% by weight by the procedure of Example 4, and the recovered granules were screened to two mesh sizes.

TABLE II

| Example | Treatment | No. insects per treatment | % Mortality After: 7 Days | 12 Days |
|---|---|---|---|---|
|  | Encapsulated B.t. (0.2%) |  |  |  |
| 6 | 50 μg/g diet | 27 | 0 | 33.3*** |
| 7 | 15 μg/g diet | 25 | 0 | 12* |
| 8 | Blank granules (control) | 30 | 0 | 0 |
|  | Amylase-treated encapsulated B.t. (0.2%) |  |  |  |
| 9 | 50 μg/g diet | 30 | 100*** | — |
| 10 | 15 μg/g diet | 30 | 60*** | 86.7*** |
| 11 | Blank granules (control) | 30 | 0 | 0 |
|  | Aqueous suspension of B.t. |  |  |  |
| 12 | 50 μg/g diet | 30 | 96.7*** | 100*** |
| 13 | 15 μg/g diet | 30 | 66.7*** | 80*** |
| 14 | Diet only (control) | 30 | 0 | 0 |
|  | Amylase-treated encapsulated B.t. (0.3%), 4-mo-old sample |  |  |  |

TABLE II-continued

| Example | Treatment | No. insects per treatment | % Mortality After: 7 Days | 12 Days |
|---|---|---|---|---|
| 15 | 50 μg/g diet | 30 | 100*** | — |
| 16 | Blank granules (control) | 30 | 0 | 0 |

*Indicates $P \leq 0.05$;
***Indicates $P < 0.001$, $\chi^2$ Tests of each treatment against its appropriate control.

TABLE III

| Example | Treatment (25 insects each) | % Mortality After: 7 Days | 12 Days | Mean survivor wt. (mg) at 12 days |
|---|---|---|---|---|
| | Encapsulated B.t. (0.3%) | | | |
| 17 | 50 μg/g diet, 10–20 mesh[a] | 0 | 16* | 5.0*** |
| 18 | 15 μg/g diet, 10–20 mesh[a] | 4 | 20* | 15.0* |
| 19 | 50 μg/g diet, 20–35 mesh[a] | 4 | 32** | 6.0*** |
| 20 | 15 μg/g diet, 20–35 mesh[a] | 0 | 16* | 11.5** |
| 21 | 15 μg/g diet, 35 mesh[a] | 4 | 16* | 5.5* |
| 22 | 15 μg/g diet, 35 mesh[a] | 0 | 24** | 5.8*** |
| 23 | Blank granules (control) | 0 | 0 | 29.1 |
| | Free B.t. suspended in diet | | | |
| 24 | 50 μg/g diet | 44*** | 72*** | 0.3*** |
| 25 | 15 μg/g diet | 0 | 28** | 0.8*** |

[a]10 mesh = 2000 microns; 20 mesh = 850 microns; 35 mesh = 500 microns.
*Indicates $P \leq 0.05$;
Indicates $P \leq 0.01$; *Indicates $P < 0.001$, based on analysis of log transformed data.

Granules of each screen size and a blank were assayed against both neonate and second instar (6-day-old) European corn borer larvae in a 24-hr exposure assay. Polyethylene cups (30 ml), each containing 5 g (about 1 cm depth) of hardened plaster of paris-charcoal mixture (15:1) saturated with water, were used to expose larvae to B.t. Larvae (15 to 30 per cup) were allowed to feed on a 250-mg dose of the encapsulated B.t. for 24 hr. Control tests against larvae feeding on starch granules containing no B.t. were run simultaneously. Each treatment consisted of a total of five exposure cups. After 24-hr exposure, mortalities were recorded, and randomly selected surviving larvae (six from each cup—30 total) were transferred to individual cups containing diet. Mortalities of the 30 larvae subsampled were recorded after 7 days, and total mortality for the treatment was calculated. After 12 days all surviving larvae remaining were individually weighed and compared to control larvae. The results are reported in Table IV below. Microscopic examination of cadavers dead for 2 or more days revealed the presence of large numbers of B.t. vegetative cells and spores. Two- to sixfold differences in mean body weights between B.t.-treated larvae and the controls are indicative of a feeding cessation response when sublethal doses of the entomopathogen are consumed.

EXAMPLE 32

To demonstrate the encapsulation procedure on a large scale, pregelatinized cornstarch (1820 9) was mixed in a planatory mixer with water (3640 ml), corn oil (145 g), and B.t. (9.78 g suspended in 728 ml water). The mixture which was kept at 100 for 18 hr produced a nonsticky mass which was coated with pearl starch (1092 g) and processed in a Waring blender to pass 14 mesh. Yields of dried product was 3100 g of which 600 g passed a 40-mesh screen and 2500 g were between 20–40 mesh.

TABLE IV

| Example | Encapsulated B.t. (0.3%) treatment | % Mortality at 7 days | Mean survivor wt. (mg) at 12 days |
|---|---|---|---|
| | Neonate larvae | | |
| 26 | <35 mesh[a] | 43.3*** | 28.7 |
| 27 | 20–35 mesh[a] | 63.3*** | 17.0*** |
| 28 | Blank granules (control) | 0 | 40.3 |
| | Second instar larvae | | |
| 29 | <35 mesh[a] | 13.3* | 36.0** |
| 30 | 20–35 mesh[a] | 43.3*** | 25.4*** |
| 31 | Blank granules (control) | 0 | 63.8 |

[a]20 mesh = 850 microns; 35 mesh = 500 microns.
*Indicates $P \leq 0.05$;
**Indicates $P \leq 0.01$;
***Indicates $P < 0.001$, based on analysis of log transformed data.

EXAMPLE 33

To demonstrate an alternate embodiment of the invention, preglatinized cornstarch (25 g) was blended with a water (50 ml)-methanol (10 ml) mixture containing corn oil (2 ml) and B.t. (158 mg). The mixture was kept at 100 for 48 hr, filtered to remove about one-third of the solvent and dried to yield a nonsticky powder passing 40 mesh containing encapsulated B.t.

EXAMPLES 34–39

A series of sprayable formulations useful for encapsulating agents in accordance with the invention were prepared by mixing pregelled corn flour (Illinois Cereal Mills) with water at concentrations ranging from 3–10%. Paste viscosities were measured over a 24-hr period using a "Brookfield LVF" viscometer at 6 rpm. At the 10% flour level, the paste approached the practical viscosity limit for field application with a commercial sprayer. When held at the initial concentrations, the pastes did not thicken with time, indicating the occurrence of little or no retrogradation. The results are reported in Table V below.

EXAMPLE 40

The long-term storage stability of B.t. encapsulated at 0.3% by weight by the method of Example 4 was determined as follows. The granular formulation was stored in a container in the laboratory at room temperature for a period of slightly more than 10 mo. A 100-mg sample of the stored product was treated with 6 ml of 0.1% α-amylase, homogenized within 1 hr, and allowed to stand for about 24 hr. After addition of 4 ml water, the homogenate was serially diluted and plated on selective agar (100 μL). The spore count taken on the 1-yr anniversary of the initial sample preparation indicated that there had been no deterioration in spore viability.

EXAMPLE 41

Encapsulated B.t. (0.3% by weight) prepared by the method of Example 4 was stored in water for a period of 7 mo. The water was replaced intermittently to remove any leachates of spores and crystals. A sample of the stored product was assayed against the European corn borer by the 24-hr exposure method described in Examples 26–31. Of 158 larvae placed into the assay, 109 were dead within 24 hr. Of 30 survivors taken in the next stage of the assay, 24 died within 4 days.

TABLE V

| Example | Flour concentration | Viscosities (cps) | | | |
| --- | --- | --- | --- | --- | --- |
| | | Initial | 3 hr | 6 hr | 24 hr |
| 34 | 3 | 50 | 40 | 50 | 50 |
| 35 | 5 | 60 | 50 | 60 | 60 |
| 36 | 7 | 80 | 80 | 80 | 80 |
| 37 | 8 | 120 | 120 | 120 | 140 |
| 38 | 9 | 230 | 240 | 260 | 250 |
| 39 | 10 | 450 | 480 | 520 | 500 |

EXAMPLES 42–47

*Autographa california* multinuclear polyhedrosis virus was encapsulated ($3 \times 10^6$ polyhedral inclusion bodies per g matrix) by the method of Example 4 and assayed against the European corn borer by the 24-hr exposure method described in Examples 26–31. The mortality rate after 7 days of 30 larvae in each of seven assays is reported below in Table VI.

TABLE VI

| Example | % Mortality at 7 days |
| --- | --- |
| 42 | 83 |
| 43 | 90 |
| 44 | 93 |
| 45 | 93 |
| 46 | 93 |
| 47 | 70 |

It is understood that the foregoing detailed description is given merely by way of illustration and that modification and variations may be made therein without departing from the spirit and scope of the invention.

We claim:

1. A method for the encapsulation of an entomopathogenic biocontrol agent comprising the steps:
   a. preparing an aqueous dispersion of a retrodegradable, amylase-digestible, pregelatinized starch having an amylose content of above about 5% and an effective amount of said biocontrol agent, wherein said biocontrol agent is a living pathogen of insects selected from the group consisting of bacteria, fungi, yeasts, viruses, microsporidians, protozoa, and phages, and wherein the relative amount of the starch with respect to the agent is sufficient to entrap the agent within a matrix of the starch;
   b. subjecting the dispersion consisting essentially of said starch, said biocontrol agent and water to gelation conditions whereby the amylose components will reassociate with one another and thereby transform said dispersion into a continuous insolubilized matrix having entrapped therein uniformly dispersed, discontinuous domains of the agent; and
   c. converting said matrix into discrete, free-flowing, nonagglomerating particles.

2. The method of claim 1 wherein the starch is chemically unmodified starch.

3. The method of claim 2 wherein the starch is pearl corn starch.

4. The method of claim 1 wherein the starch solids content of the dispersion is in the range of about 25–40% by weight and said matrix is recovered as a dry granule.

5. The method of claim 1 wherein the starch is a chemically degraded starch at a solids content in the dispersion in the range of 1–10%, whereby said dispersion is a sprayable liquid.

6. The product produced by the method of claim 1.
7. The product produced by the method of claim 2.
8. The product produced by the method of claim 3.
9. The product produced by the method of claim 4.
10. The product produced by the method of claim 5.

* * * * *